United States Patent [19]

Abts

[11] 4,217,781
[45] Aug. 19, 1980

[54] ULTRASONIC PARTICULATE SENSING
[75] Inventor: Leigh R. Abts, Providence, R.I.
[73] Assignee: Micro Pure Systems, Inc., North Providence, R.I.
[21] Appl. No.: 31,066
[22] Filed: Apr. 18, 1979
[51] Int. Cl.³ ............................................. G01N 29/02
[52] U.S. Cl. ...................................... 73/632; 73/642; 73/644
[58] Field of Search ............. 73/642, 632, 644, 194 A; 128/214 E; 340/8 L; 310/335

[56] References Cited
U.S. PATENT DOCUMENTS

| 3,821,834 | 7/1974 | McElroy | 73/632 |
| 3,876,890 | 4/1975 | Brown et al. | 73/194 A |
| 4,112,773 | 9/1978 | Abts | 73/642 |

FOREIGN PATENT DOCUMENTS 2240342  3/1974  Fed. Rep. of Germany .

Primary Examiner—Anthony V. Ciarlante

[57] ABSTRACT

A pulse echo device for obtaining information about matter discontinuities in flowing fluid with a sidewall spaced from and surrounding the walls of a transducer situated with respect thereto in such a way that over half the waves radiating from the transducer walls strike the surrounding sidewall at angles less than 90° thereby improving sensitivity and increasing signal-to-noise ratio.

5 Claims, 4 Drawing Figures

ULTRASONIC PARTICULATE SENSING

FIELD OF THE INVENTION

This invention relates to obtaining information about matter discontinuities in flowing fluid streams, for example, the size, number and type of such discontinuities.

BACKGROUND OF THE INVENTION

The background of the invention is fully set out in my U.S. Pat. No. 4,112,773, and my U.S. Pat. application Ser. No. 951,614, filed Oct. 16, 1978, both hereby incorporated by reference.

SUMMARY OF THE INVENTION

I have discovered that discontinuities in flowing fluids can be detected with improved sensitivity and greater signal-to-noise ratio when a sidewall spaced from and surrounding the walls of a transducer is situated with respect thereto in such a way that over half the waves radiating from the transducer walls strike the surrounding sidewall at angles different from 90°. In preferred embodiments, the transducer is rectangular with rounded ends, the surrounding sidewall is circular, sound absorptive material covers the transducer, and the sound absorptive material has the same energy impedance as that of the surrounding sidewall material.

PREFERRED EMBODIMENT

We turn now to the structure and operation of a preferred embodiment, after first briefly describing the drawings.

DRAWINGS

STRUCTURE

Figure 1:
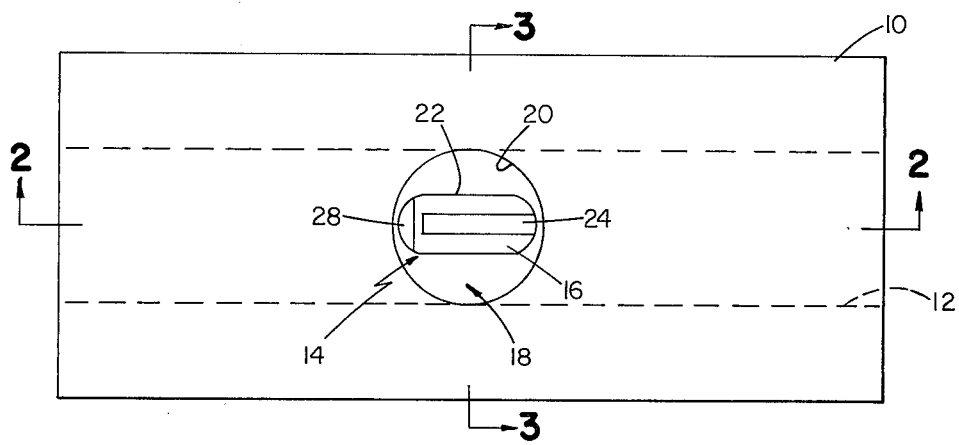
FIG. 1 is a plan view of said embodiment, with the epoxy backing removed from the ultrasonic transmitter-receiver.
Figure 2:
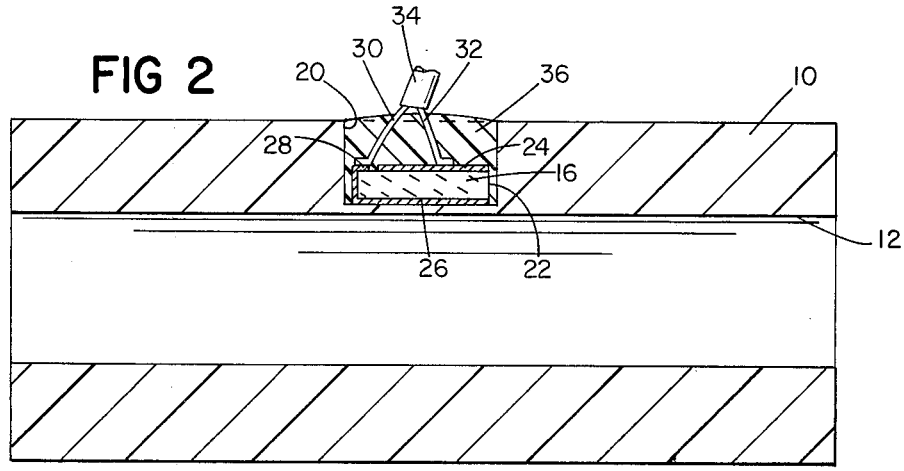
FIG. 2 is a cross sectional view at 2—2 of FIG. 1.
Figure 3:
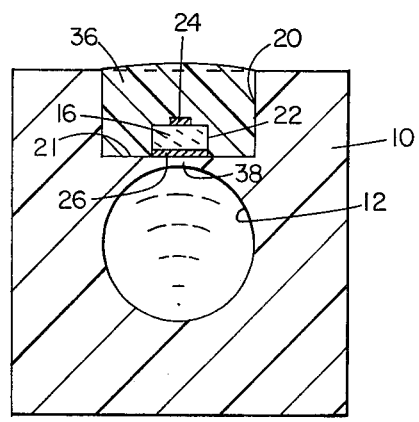
FIG. 3 is a cross sectional view at 3—3 of FIG. 1, with the wires removed from the transducer.

Referring to FIGS. 1-3, there is shown a tube 10 of methyl methacrylate. Tube 10 has an interior bore 12 with a 1 inch diameter. Hoses or other couplings (not shown) are provided on the tube ends for connection with a fluid circuit (not shown).

Ultrasonic transmitter-receiver 14 is midway between the ends of tube 10. Ultrasonic transmitter-receiver 14 includes piezoelectric crystal 16 mounted in blind hole 18. Blind hole 18 has a cylindrical sidewall 20 and a flat bottom 21. The bottom 21 of hole 18 extends to 1.0. mm from interior bore 12. The hole 18 has a diameter of 1 inch.

Crystal 16 (7.5 megahertz) has two parallel sides and two rounded endwalls. Crystal 16 is positioned in blind hole 18 so that it is longitudinally aligned with bore 12. The crystal 16 does not contact the sidewall 20 of blind hole 18. Wall 22 of crystal 16 is spaced apart from sidewall 20 of the blind hole 18. Crystal 16 also has an upper electrode 24 and a lower electrode 26. The electrodes 24, 26 are of gold. Upper electrode 24 is 50 mils wide and extends axially down the center of the crystal 16. Lower electrode 26 covers the entire lower surface of crystal 16 and a small portion 28 across the width of the upper surface. The lower electrode 26 is more than twice as wide as the upper electrode 24. Wires 30, 32 of a lead 34 are soldered to electrodes 24, 26.

An epoxy backing 36 covers the crystal 16 and fills the remainder of the blind hole 18. The epoxy backing 36 is tungsten-loaded Araldite epoxy mixed with polyamide hardener. The ratio of epoxy to tungsten is 1:1 by weight. A lens 38 integral with tube 10 is below crystal 16. One surface of the lens is formed by the concavity of the bore 12. The other surface of the lens 38 is formed by the bottom 21 of the blind hole 18.

OPERATION

In operation, the crystal may as desired be energized to give an output for 1.13 microseconds, to transmit through its associated lens an ultransonic pulse of that duration. Any reflection received by the crystal may be sent to a receiver (i.e., Micro Pure Monitor 1100) and then displayed on an oscilloscope. The shapes of the curves generated provide information about discontinuities in fluid flowing through the passage. Thus number of peaks reflects number of particles and increased amplitude reflects increased particle size, particularly in situations in which only one particle is ordinarily within the field of focus at any given time. The phase of the first returning cycle also contains important information. A gas bubble causes an inversion of the first cycle. A solid particle does not. The duration of the returning signal can also be used to distinguish a gas bubble from a solid particle. The returning signal of the gas bubble has a shorter duration.

When energized, the crystal 16 produces both longitudinal waves and surface waves. The longitudinal waves radiate from the bottom of the crystal. These waves are focused by the lens 38, travel into the bore 12 and are reflected by the discontinuities in the flowing fluid. It is the reflected longitudinal waves which contain the important information.

Surface waves are generated from the wall 22 of the crystal 16 and radiate outwardly. The signal-to-noise ratio is improved if the surface waves are not reflected back to the crystal 16.

Figure 4:
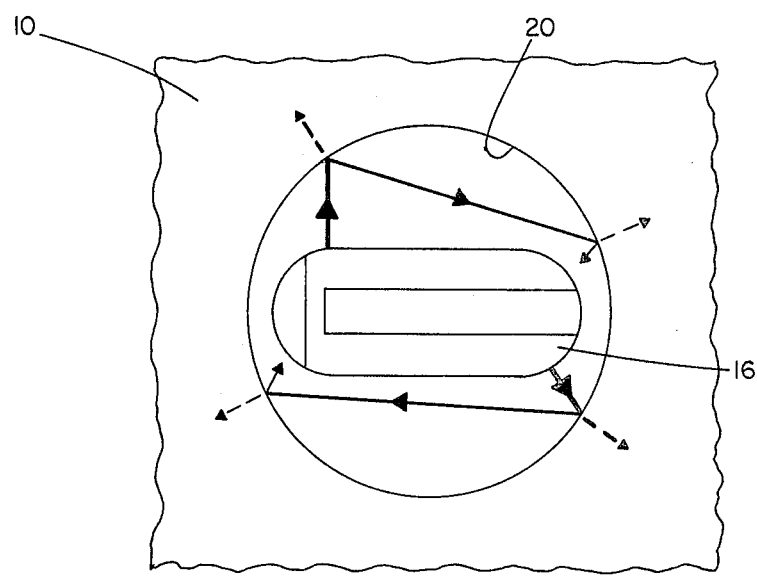
FIG. 4 is an enlarged top view of the transducer with representative energy wave emitting therefrom.

The amount of reflected surface wave decreases as the angle at which the wave strikes the sidewall decreases from an angle of 90 °. Because of the spacial arrangement between the crystal wall 22 and blind hole sidewall 20, most of the surface waves strike the sidewall 20 at angles less then 90°. Most of these surface waves then pass into the tube 10. Further, as shown in FIG. 4, most of the portions of the waves not passed into the tube must strike the sidewall 20 at least one more time before they are reflected back to the crystal 16, and each time a wave strikes the sidewall, more of it passes into the tube 10. Very little of these surface waves are reflected from the sidewall 20 back to the crystal 16.

The epoxy backing 36 has approximately the same sound impedance as that of the tube material. Sound waves only reflect at the interface between two materials with different sound impedances. This impedance matching also reduces the amount of reflected surface waves and improves the signal-to- noise ratio.

An air-backed crystal has a narrow bandwidth. It can be used to detect small discontinuities, but it cannot detect the first cycle of the returning signal more than 50% of the time nor can it accurately distinguish between the durations of the returning signals. The epoxy backing of this invention broadens the bandwidth of the crystal 16 and enables it to reliably detect the duration of the returning signal or the first cycle of the returning signal. Some sensitivity is lost by broadening the bandwidth, but a portion of the lost sensitivity can be regained by driving the crystal at one of its bandwidth frequency peaks.

OTHER EMBODIMENTS

Other embodiments of the invention will occur to those skilled in the art. For example, the bore could be closed at one end, forming a bottle chamber. A pharmaceutical bottle could be inserted into this chamber. The bottle could be acoustically coupled to the chamber walls by filling the remainder of the chamber with liquid. The liquid in the bottle could then be tested for the presence of particles.

What is claimed is:

1. A pulse echo device for obtaining information about matter discontinuities in a flowing fluid comprising:
    a transducer for producing energy waves,
        said transducer having a sidewall,
    a sidewall surrounding and spaced apart from but in close proximity to said transducer sidewall whereby the spatial relationship between said surrounding sidewall and said transducer sidewall is such that over half the energy waves radiating from said transducer sidewall strike said surrounding sidewall at least twice and at angles of less than 90° thereby damping the waves before the waves can reflect back to strike said transducer sidewall.

2. The device of claim 1 wherein said transducer is rectangular with rounded ends and said surrounding sidewall is circular.

3. The device of claim 1 further comprising an epoxy backing partially disposed between said transducer sidewall and said surrounding sidewall, said epoxy backing having the same energy impedance as the material of said surrounding sidewall.

4. The device of claim 3 wherein said epoxy backing partially contacts and extends above a side of said transducer away from the flowing fluid.

5. The device of claim 4 wherein said epoxy backing is tungsten loaded epoxy with the ratio of epoxy to tungsten being 1:1 by weight and the material of said surrounding sidewall is methyl melthacrylate.

* * * * *